US010442751B2

(12) United States Patent
Hanan et al.

(10) Patent No.: US 10,442,751 B2
(45) Date of Patent: Oct. 15, 2019

(54) METHOD FOR PREPARING SUBSTITUTED ALKYL CYCLOALKANONES

(71) Applicant: SYMRISE AG, Holzminden (DE)

(72) Inventors: Atia Hanan, Rostock (DE); Reinhard Eckelt, Rostock (DE); Angela Koeckritz, Berlin (DE); Johannes Panten, Hoexter (DE); Peter Esser, Bevern (DE); Oskar Koch, Goettingen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/547,435

(22) PCT Filed: Jan. 13, 2016

(86) PCT No.: PCT/EP2016/050561
§ 371 (c)(1),
(2) Date: Jul. 28, 2017

(87) PCT Pub. No.: WO2016/120070
PCT Pub. Date: Aug. 4, 2016

(65) Prior Publication Data
US 2018/0022683 A1    Jan. 25, 2018

(30) Foreign Application Priority Data

Jan. 30, 2015 (EP) .................................. 15153282

(51) Int. Cl.
C07F 9/09 (2006.01)
C07C 45/69 (2006.01)
C07C 68/00 (2006.01)
C07C 69/12 (2006.01)
C07C 69/14 (2006.01)
C07C 69/96 (2006.01)
C07C 303/24 (2006.01)
C07C 49/497 (2006.01)
C07C 49/503 (2006.01)
C07C 51/353 (2006.01)
C07C 67/293 (2006.01)

(52) U.S. Cl.
CPC ............ C07C 67/293 (2013.01); C07C 45/69 (2013.01); C07C 51/353 (2013.01); C07C 68/00 (2013.01); C07C 69/12 (2013.01); C07C 303/24 (2013.01); C07F 9/091 (2013.01); C07C 49/497 (2013.01); C07C 49/503 (2013.01); C07C 2601/18 (2017.05); C07C 2601/20 (2017.05); Y02P 20/582 (2015.11)

(58) Field of Classification Search
None
See application file for complete search history.

(56) References Cited

U.S. PATENT DOCUMENTS

| 3,856,815 | A | 12/1974 | Hopp et al. |
| 4,268,445 | A | 5/1981 | Kropp et al. |
| 4,387,250 | A | 6/1983 | Uijttewaal et al. |
| 6,380,119 | B1 | 4/2002 | Grosch et al. |
| 6,710,002 | B2 | 3/2004 | Grosch et al. |
| 2002/0165416 | A1* | 11/2002 | Ishii ....................... C07C 45/33 568/398.8 |

FOREIGN PATENT DOCUMENTS

| DE | 19853862 | 6/1999 |
| JP | S6279848 A | 4/1987 |
| WO | 8504821 A1 | 11/1985 |

OTHER PUBLICATIONS

Rigby ("Alkoxy radical accelerated beta-fragmentation of alcohols and lactols" Tetrahedron Letters, 42, 2001, 2047-2049).*
Hajek ("Radical Addition of Ketones to Alkenes Initiated by Transition Metal Oxides" Synthesis, 1976, p. 315-318) (Year: 1976).*
https://www.masterorganicchemistry.com/2010/10/06/functional-groups-organic-chemistry/, downloaded on Jul. 19, 2018 (Year: 2018).*
http://chemed.chem.purdue.edu/genchem/topicreview/bp/2organic/2org_frame.html (Year: 2018).*
https://nssdc.gsfc.nasa.gov/planetary/factsheet/earthfact.html, downloaded on Jul. 23, 2018 (Year: 2018).*
Song ("A high performance oxygen storage material for chemical looping processes with CO2 capture" Energy and Environmental Science, 2013, 6, p. 288-298) (Year: 2013).*
Rauf ("Preparation and characterization of cyclic-ketone derivatives of methyl-undec-10-enoate and their cyclocondensation with mercaptoacetic acid" Indian Journal of Chemistry, vol. 44B, Aug. 2005, p. 1644-1648) (Year: 2005).*
International Search Report for PCT/EP2016/050561, English Translation attached to original, Both completed by the European Patent Office on May 10, 2016, All together 5 Pages.
Dennis P. Curran, The Design and Application of Free Radical Chain Reactions in Organic Synthesis. Part 2, Department of Chemistry, University of Pittsburgh, PA 15260, USA, 489-513, (7), 1988.
Hwu, Jih Ru, Buh-Luen Chen, and Shui-Sheng Shiao. "Silicon-Promoted Carbon-Carbon Bond Formation between Ketones and Allyl-or Vinylsilanes Catalyzed by Manganese (IV) Dioxide." The Journal of Organic Chemistry 60.8 (1995): 2448-2455.
JP 2017540273 Notice of Refusal, dated Feb. 26, 2019, English translation included, 11 pages.

* cited by examiner

*Primary Examiner* — Amy C Bonaparte
(74) *Attorney, Agent, or Firm* — Brooks Kushman P.C.

(57) ABSTRACT

The present invention relates to a method for producing a substituted alkyl cycloalkanone, comprising the alkylation of a cycloalkanone with an alkene derivative in the presence of a metal oxide, where n is 2 to 20, m is 0 to 10, and R is a functional group.

13 Claims, No Drawings

METHOD FOR PREPARING SUBSTITUTED ALKYL CYCLOALKANONES

CROSS-REFERENCE TO RELATED APPLICATION

This application is the U.S. national phase of PCT Application No. PCT/EP2016/050561 filed on Jan. 13, 2016, which claims priority to EP Patent Application No. 15153282.7 filed on Jan. 30, 2015, the disclosures of which are incorporated in their entirety by reference herein.

FIELD OF THE INVENTION

The present invention relates to the field of the preparation of substituted alkyl cycloalkanones of the formula I

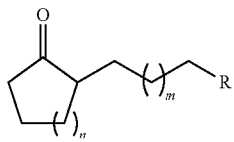

Formula I

PRIOR ART

Substituted alkyl cycloalkanones of the formula I are important intermediates, particularly for the synthesis of musk scents. Musk scents are an important component of perfumes.

According to DE19853862 A1, selected compounds of the formula I are prepared by free-radical addition of hydroxyalkenes or acyloxyalkenes to cyclic ketones using a suitable organic radical chain initiator. Many of the radical chain initiators used have disadvantages when used. They must, for example, be fed continuously to the reactor, are irreversibly consumed during the reaction and promote the formation of reaction by-products, particularly of polymers. The formation of polymers is particularly disadvantageous in continuous processes since they are carried out over very long periods, so that even a low polymer formation rate has a disadvantageous effect. The reaction must be interrupted from time to time due to increasing viscosity or due to increasing deposits. Moreover, many of the radical chain initiators expressly mentioned have disadvantageous properties, such as high flammability, formation of explosive mixtures, irritating or toxic gases or intermediates. These properties mean that the safety-related expenditure in carrying out the reaction has to be very high. Apart from the desired substituted monoalkyl cycloalkanones, the reaction also produces high proportions of substituted di-, tri- and tetraalkyl cycloalkanones, as a result of which consumption of the starting products is enhanced and they can no longer be recovered. Due to the high temperatures to be employed in carrying out the process, it is recommended to operate under high pressure in order to reduce the loss of low-boiling substances. This requires special pressure-tight equipment.

OBJECT OF THE INVENTION

The object of the present invention is to prepare substituted alkyl cycloalkanones of the formula I at a high rate, high yield, high selectivity, lower energy consumption, lower raw material consumption and with fewer by-products, and/or to increase the safety of the process.

DESCRIPTION OF THE INVENTION

The invention relates to a method for preparing a substituted alkyl cycloalkanone of the formula I

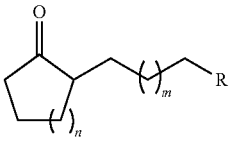

Formula I comprising the alkylation of a cycloalkanone of the formula II

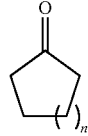

Formula II with an alkene derivative of the formula III

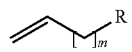

Formula III in the presence of a metal oxide, where n is 2 to 20, m is 0 to 10 and R is a functional group.

Compounds of the formula I may be those where n=3 to 15 and m=0 to 5. R may be a hydroxyl, carboxyl, carbonyloxyalkyl, formyloxy, alkylcarbonyloxy, arylcarbonyloxy or benzylcarbonyloxyalkyl group or one of the following groups:

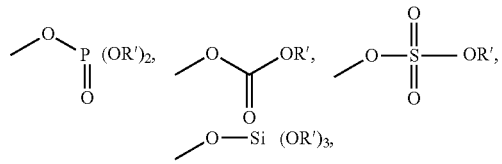

where R' is an alkyl, aryl, heteroaryl, alkylaryl or cycloalkyl radical.

The variables of the preferred compounds of the formulae II and III are correspondingly analogous.

Surprisingly, it has been found that no polymers of compounds of the formula II can be detected during the performance of the method according to the invention so that the method can be carried out continuously and without interruption over a very long period of time. In the context of the invention, polymers are understood to mean macromolecules having a monomer number greater than or equal to 5. In addition, the proportion of the substituted di-, tri- and tetraalkyl cycloalkanones formed is greatly reduced, as a result of which the consumption of the reactants is reduced, so that more reactants can be recovered and reused. The metal oxides can also be reoxidized and reused after reduction.

Compounds of the formula I are, for example, 2-(3-hydroxypropyl)cyclododecanone and 2-(3-acetoxypropyl)cyclododecanone.

Compounds of the formula II are, for example, cyclohexanone, cyclooctanone, cyclododecanone and cyclohexadecanone.

Compounds of the formula III are, for example, allyl alcohol, allyl acetate, allyl formate, allyl propionate, allyl benzoate and allyl phenylacetate.

The method according to the invention can be readily carried out with metal oxides selected from the group of copper oxides, iron oxides, manganese oxides, indium oxides, cobalt oxides, silver oxides and mixtures thereof. The method can be particularly readily carried out with metal oxides selected from $Ag_2O$, $CuO$, $Fe_2O_3$, $Fe_3O_4$, $CuFe_2O_4$, $Co_3O_4$, $CoO$, $MnO_2$, $In_2O_3$ and mixtures thereof.

Under the reaction conditions, silver oxides such as $Ag_2O$ form silver mirrors or very finely divided silver particles, which are strongly eroded into the reaction medium, so that the expenditure for recovery, in particular the separation from the remaining constituents and the cleaning of the plant, is increased. This disadvantage does not exist when using copper oxides, iron oxides, manganese oxides, indium oxides, cobalt oxides and mixtures thereof and/or CuO, $Fe_2O_3$, $Fe_3O_4$, $CuFe_2O_4$, $Co_3O_4$, CoO, $MnO_2$, $In_2O_3$ and mixtures thereof, they do not erode in the process, or only slightly, and do not form metal mirrors. The expenditure for recovery and plant cleaning is consequently lower.

The metal oxides may be used preferably as powders or granules. The metal oxides may also be applied to a suitable inorganic support material, such as aluminum oxide.

It is advantageous if the method proceeds at temperatures in the range of 100 to 250° C., preferably in the range of 150 to 220° C. and particularly preferably in the range of 160 to 190° C. The method can be carried out at atmospheric pressure or optionally under positive pressure.

In the batch process, the use concentration of the metal oxide can be 1-50 mol % based on the amount of cycloalkanone of the formula II and preferably 5-25 mol %, based on the amount of cycloalkanone of the formula II. In the continuous process, it is more appropriate to specify the space velocity (quotient of the continuously supplied mass flow of compounds of the formulae II and III and the mass of the metal oxide). It is preferably 0.01 to 1 per hour and particularly preferably 0.02 to 0.5 per hour.

The molar ratio of cycloalkanone of the formula II to alkene derivative of the formula III may be between 1:1 and 10:1 and preferably between 2:1 and 8:1.

The method may be carried out continuously or batchwise. To carry out the batchwise method, a discontinuous stirred tank reactor for example is suitable. Suitable for the continuous method is, for example, a continuous tubular reactor, stirred tank reactor, fixed-bed reactor or trickle-bed reactor.

After the method has been carried out, a product mixture is present which, depending on the duration and process parameters applied, is a mixture with a varying concentration of the reactants and products. The product mixture can be separated by suitable separation methods, in particular by distillation, whereby the already high purity of the desired alpha-monoalkyl products can be further increased and, optionally, unreacted reactants can be recovered and reused.

The metal oxide used is reduced by the reaction. The reduced metal oxide is the metal formed from the metal oxide, metal oxide of a lower oxidation state or mixtures thereof. In the method, the reduced metal oxide forms on the surface of the solid metal oxide.

A further advantage of the invention is that the metal oxide can be regenerated (reoxidized) after it has been reduced by the reaction according to the invention. The reoxidation can be effected by contacting the reduced metal oxide with an oxygen-containing gas. The reduced metal oxide can be reoxidized particularly effectively by means of a heated oxygen-containing gas stream, the gas stream having a temperature of 100 to 500° C. The oxygen content of the gas may comprise at least 0.1 vol % oxygen, based on the total amount of oxygen-containing gas, determined at 20° C. and 1013.25 hPa, in order to allow the reoxidation to proceed in a short time.

The reduced metal oxide may be separated from the product mixture in order to reoxidize it prior to contact with the oxygen-containing gas. In this procedure, the preferred oxygen content of the oxygen-containing gas is at least 17 vol % and its temperature is between 150 and 500° C., in order to enable particularly rapid reoxidation. The metal oxide regenerated in this manner shows the same activity as the metal oxide originally used during reuse in the reaction according to the invention. This procedure can, for example, be used in a batchwise process. It is also suitable for a continuous process, wherein, at the beginning of the process for example, at least two mutually separate portions of metal oxide are present. Firstly, one of the portions of the metal oxide is charged with a reactant stream and a product stream is removed. After partial or complete reduction of the metal oxide, the reactant stream is passed to a different portion of the metal oxide and the reaction is carried out thereover. Meanwhile, the first portion, which is now reduced to a certain degree, is separated from the product mixture and reoxidized with the oxygen-containing gas stream. Subsequently, the process can be switched to the first or a further portion of metal oxide and the process can thus be operated continuously.

The process can be operated particularly advantageously if an oxygen-containing gas stream is introduced into the reactor during the course of the alkylation reaction. The oxygen-containing gas stream should come into contact with the reduced metal oxide. The process can thus be continuously operated with little effort over a very long time period, with appropriate continuous feed of the reactants and removal of the product mixture. Oxidative and reductive processes occur simultaneously. In this process, the preferred oxygen content of the oxygen-containing gas is 0.1 to 20 vol %, and particularly preferably 3 to 16 vol %, and therefore particularly few by-products from free-radical side reactions are formed and rapid reoxidation of the reduced metal oxide is enabled. In this case, the temperature of the oxygen-containing gas stream should be identical to, or close to, the temperature in the reactor.

The invention also comprises a product prepared by the method according to the invention. The product can be characterized in particular by the fact that it comprises a very low concentration of substituted di-, tri- and tetraalkyl cycloalkanones.

Example 1

A stirred tank reactor is filled with 45.5 g of cyclododecanone (CDD) and 5.01 g of allyl acetate (AlAc) and copper oxide (CuO) (molar ratio CDD:AlAc 3:1) and the mixture is stirred at 160° C. for 24 h. The copper oxide (CuO) was then filtered off and the reaction mixture analyzed by gas chromatography and the selectivity of the method calculated using the formula S=(amount of alpha-monoalkyl product formed)/(amount of CDD used). It is 70%.

In Example 1 of DE 19853862 (comparative example from the prior art to date), the selectivity is only 12%.

Consequently, in the method according to the invention, substantially more of the desired alpha-monoalkyl product is formed relative to the CDD used.

Example 2

A fixed-bed glass reactor with a diameter of 1.9 cm, equipped with a metering device for liquids and gases at the top of the reactor and a double-jacketed heater and a device for collecting the product mixture at the reactor outlet, is filled with the provided amount of granulated CuO (50.7 g; 17.5 ml; particle diameter 0.71-1.25 mm). The granules are obtained from pulverulent CuO by pressing, comminuting the pellets and sieving the desired fraction. Above and below the initiator granules, the free volume of the reactor interior is filled with inert corundum particles to minimize the dead volume and fix the initiator. The mixture of cyclododecanone (CDD) and allyl acetate (AlAc) at the ratio 1:7.5 is allowed to flow over the initiator bed heated to 180° C. at a flow rate of 2.9 g/h. At the same time, air is passed through the reactor bed at a rate of 2 ml/min. The product mixture is collected at the reactor outlet and the composition thereof is determined by gas chromatographic analysis. The selectivity for the monoalkylated product is 75.3%. Unreacted CDD is removed from the products by distillation and recycled.

The invention claimed is:

1. A method for preparing a substituted alkyl cycloalkanone of formula I

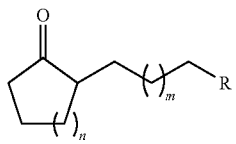

Formula I comprising the alkylation of a cycloalkanone of formula II

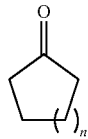

Formula II with an alkene derivative of formula III

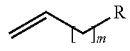

Formula III in the presence of a metal oxide, where n is 2 to 20, m is 0 to 10 and R is a hydroxyl, carboxyl, carbonyloxyalkyl, formyloxy, alkylcarbonyloxy, arylcarbonyloxy or benzylcarbonyloxyalkyl group or is one of the following groups:

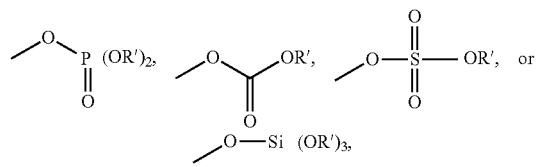

wherein R' is an alkyl, aryl, heteroaryl, alkylaryl or cycloalkyl radical; and wherein the metal oxide is a copper oxide, iron oxide, manganese oxide, indium oxide, cobalt oxide, or a mixture thereof.

2. The method as claimed in claim 1, wherein n is 3 to 15 and m is 0 to 5.

3. The method as claimed in claim 1, wherein the metal oxide is $CuO$, $Fe_2O_3$, $Fe_3O_4$, $CuFe_2O_4$, $Co_3O_4$, $CoO$, $MnO_2$, $In_2O_3$ or mixtures thereof.

4. The method as claimed in claim 1, wherein the alkylation is conducted at a temperature in the range of 100 to 250° C.

5. The method as claimed in claim 1, wherein the molar ratio of the cycloalkanone of formula II to the alkene derivative of formula III is between 1:1 to 10:1.

6. The method as claimed in claim 1, wherein metal oxide reduced during the alkylation reaction is reoxidized by an oxygen-containing gas.

7. The method as claimed in claim 6, wherein the oxygen-containing gas comprises at least 0.1 vol % oxygen, based on the total volume of oxygen-containing gas, determined at 20° C. and 1013.25 hPa.

8. The method as claimed in claim 6, comprising introducing a stream of the oxygen-containing gas to the alkylation reaction.

9. The method of claim 1, wherein the method is carried out batchwise.

10. The method of claim 1, wherein the method is carried out continuously.

11. The method as claimed in claim 1, wherein the alkylation is conducted at a temperature in the range of 150 to 220° C.

12. The method as claimed in claim 1, wherein the alkylation is conducted at a temperature in the range of 160 to 190° C.

13. The method as claimed in claim 1, wherein the molar ratio of the cycloalkanone of formula II to the alkene derivative of formula III is between 2:1 to 8:1.

* * * * *